(12) United States Patent
Adachi et al.

(10) Patent No.: US 6,359,143 B1
(45) Date of Patent: Mar. 19, 2002

(54) HETEROCYCLE-BEARING THIO PHENOL COMPOUNDS, INTERMEDIATES FOR THE PREPARATION OF THE SAME AND PROCESSES FOR THE PREPARATION OF BOTH

(75) Inventors: Hiroyuki Adachi, Odawara; Takahiro Sagae, Nakagou-mura; Toshio Aihara, Hiratsuka, all of (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 09/719,021

(22) PCT Filed: Jun. 3, 1999

(86) PCT No.: PCT/JP99/02968

§ 371 Date: Dec. 5, 2000

§ 102(e) Date: Dec. 5, 2000

(87) PCT Pub. No.: WO99/64404

PCT Pub. Date: Dec. 16, 1999

(30) Foreign Application Priority Data

Jun. 5, 1998 (JP) ............ 10-158130
Jul. 13, 1998 (JP) ............ 10-197776

(51) Int. Cl.$^7$ ............ C07D 231/12; C07D 261/08; A01N 43/56; A01N 43/80

(52) U.S. Cl. ............ 548/247; 548/377.1; 504/138; 504/139

(58) Field of Search ............ 548/247, 377.1

(56) References Cited

U.S. PATENT DOCUMENTS 5,846,907 A   12/1998   von Deyn et al.
5,939,360 A   8/1999   Adachi et al.

FOREIGN PATENT DOCUMENTS

WO   WO97/46530   12/1997

OTHER PUBLICATIONS

Tetrahedron Letters 31, 3421 (1990).
J. Org. Chem. 54, 4704 (1989).
J. Org. Chem. 50, 4105–4107 (1985).
J. Org. Chem. 55, 157–172 (1990).
PCT International Preliminary Report PCT/JP99/02968.

*Primary Examiner*—Floyd D. Higel
*Assistant Examiner*—Kamal Saeed
(74) *Attorney, Agent, or Firm*—Dennis G. LaPointe; Mason & Assoc., P.A.

(57) ABSTRACT

Novel thio phenol compounds bearing heterocyclic groups as the substituent, useful as intermediates for the preparation of agricultural chemicals, particularly herbicides; intermediates for the preparation of the same; and processes for the preparation of both as represented by reaction formula (I), herein $R^1$ is $C_1$–$C_4$ alkyl; $R^2$ is hydrogen or $C_1$–$C_4$ alkyl; $R^3$ is hydrogen cyano, amido, $C_1$–$C_4$ alkylcarbonyl or $C_1$–$C_4$ alkoxycarbonyl; $R^4$ is $C_1$–$C_4$ alkyl; and Q is isoxazolyl or the like.

6 Claims, No Drawings

HETEROCYCLE-BEARING THIO PHENOL COMPOUNDS, INTERMEDIATES FOR THE PREPARATION OF THE SAME AND PROCESSES FOR THE PREPARATION OF BOTH

This application is a 371 of PCT/JP99/02968 filed on Jun. 3, 1990.

1. Field of the Invention

The present invention relates to a novel thiophenol compound substituted with a hetero ring, which is useful as an intermediate to produce agrochemicals, particularly herbicides, an intermediate to produce the said compound, and processes for their preparation.

2. Background Art

The thiophenol compounds substituted with hetero rings of the present invention are important as intermediates to produce benzoyl pyrazole compounds with herbicidal activities, which are disclosed in, for example, WO 96/26206, WO 97/41118 and WO 97/46530.

With regard to reactions to synthesize cyclohexenone derivatives from enol lactones, similar to processes for the preparation of the cyclohexenone compounds of the present invention, for example, a reaction of an enol lactone with a lithioacetate (Reaction Scheme A below) is described in Tetrahedron Letters 31, 3421 (1990) and a reaction between an enol lactone and a Grignard reagent (Reaction Scheme B below) in J. Org. Chem. 54, 4704 (1989).

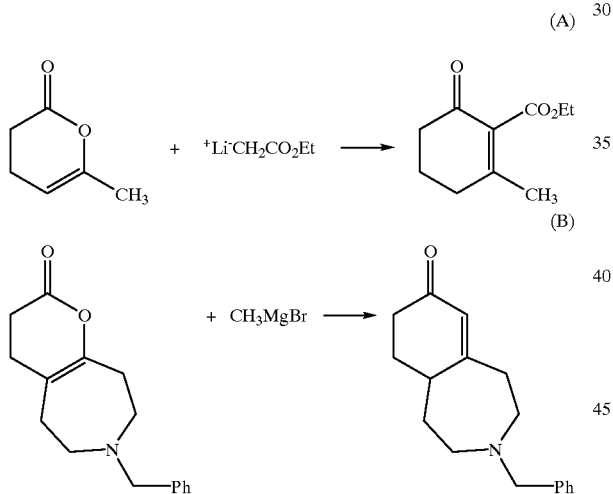

There are, however, no reports on direct reactions between enol lactones and nitrogen containing hetero ring compounds such as isoxazole.

DISCLOSURE OF THE INVENTION

It is an object of the present invention to provide novel thiophenol compounds substituted with hetero rings, which are useful as intermediates to produce agrochemicals and medicines, particularly compounds with herbicidal activities, intermediates to prepare them, and simpler and more economically advantageous processes for the preparation of thiophenol compounds substituted with hetero rings, which require multistage processes.

The present invention relates to 1. thiophenol compounds substituted with hetero rings represented by Formula (1)

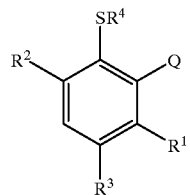

[wherein $R^1$ is $C_{1-4}$ alkyl;

$R^2$ is hydrogen or $C_{1-4}$ alkyl;

$R^3$ is hydrogen, cyano, amide, $C_{1-4}$ alkylcarbonyl or $C_{1-4}$ alkoxycarbonyl;

$R^4$ is $C_{1-4}$ alkyl; and

Q is the following Q1, Q2 or Q3

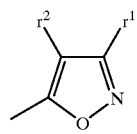

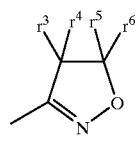

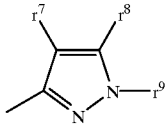

(wherein $r^1$ to $r^9$ are, each independently, hydrogen or $C_{1-4}$ alkl, or $r^3$ and $r^5$ may join to form a bond)]; and 2. cyclohexenone compounds, intermediates to produce the said compounds, represented by Formula (2)

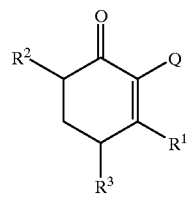

(wherein $R^1$, $R^2$, $R^3$ and Q are as defined above);

3. processes for the preparation of thiophenol compounds substituted with hetero rings, represented by the above Formula (1), characterized in reacting a cyclohexenone compound of the above Formula (2) with an alkane thiol of Formula $R^4SH$ (wherein $R^4$ is as defined above) to give a compound represented by Formula (3)

(3)

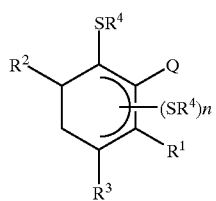

(wherein $R^1$ to $R^4$ and Q are as defined above; n is 0, 1 or 2; and the compound of Formula (3) is either a compound of the following Formula (3-1), (3-2), (3-3) or (3-4))

(3-1)

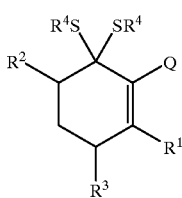

(3-2)

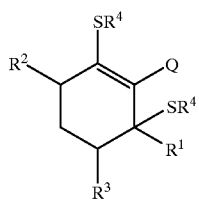

(3-3)

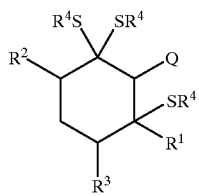

(3-4)

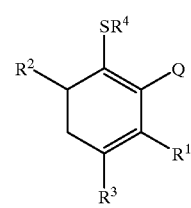

followed by dehydrogenation;
4. compounds represented by Formula (4)

(4)

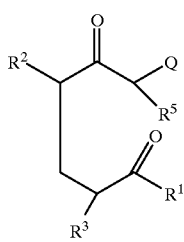

(wherein $R^1$ to $R^3$ are as defined above; and $R^5$ is hydrogen, cyano, $C_{1-4}$ alkylcarbonyl or $C_{1-4}$ alkoxycarbonyl);

5. processes for the preparation of compounds represented by the above Formula (4), characterized in reacting an enol lactone of Formula (5)

(5)

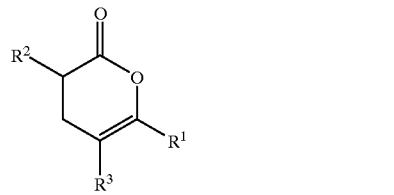

(wherein $R^1$ to $R^3$ are as defined above) with a compound of Formula Q—$CH_2R^5$ (wherein Q and $R^5$ are as defined above); and 6. processes for the preparation of cyclohexenone compounds represented by the above Formula (2), characterized in reacting an acid or a base on a compound of the above Formula (4).

An outline of the present invention may be represented by the following reaction scheme:

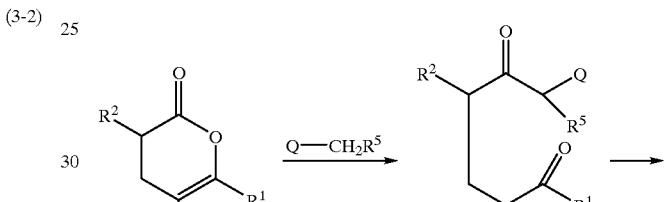

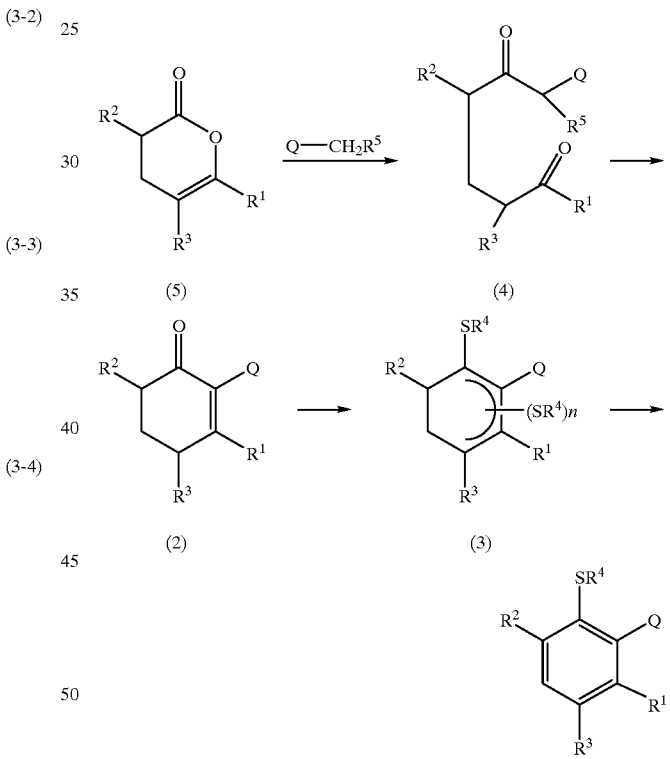

(wherein $R^1$ to $R^5$, n and Q are as defined above).

The present invention is further described in detail in the following.

IMPLEMENTATION OF THE INVENTION

In the definitions of the compounds represented by the above Formulae (1), (2), (3), (4) and (5), $R^1$ is $C_{1-4}$ alkyl such as methyl, ethyl, propyl, isopropyl, n-butyl, isobutyl, s-butyl and t-butyl;

$R^2$ is hydrogen, or $C_{1-4}$ alkyl such as methyl, ethyl, propyl, isopropyl, n-butyl, isobutyl, s-butyl and t-butyl;

$R^3$ is hydrogen, cyano, amide, $C_{1-4}$ alkylcarbonyl such as acetyl, propionyl, butyryl, isobutyryl, valeryl, isovaleryl and pivaloyl, or $C_{1-4}$ alkoxycarbonyl such as methoxycarbonyl, ethoxycarbonyl, propoxycarbonyl, isopropoxycarbonyl, butoxycarbonyl, isobutoxycarbonyl, s-butoxycarbonyl and t-butoxycarbonyl;

$R^4$ is $C_{1-4}$ alkyl such as methyl, ethyl, propyl, isopropyl, n-butyl, isobutyl, s-butyl and t-butyl;

Q is either a group of the following Q1, Q2 or Q3

Q1:

Q2:

Q3:

wherein $r^1$ to $r^9$ are, each independently, hydrogen, or $C_{1-4}$ alkyl such as methyl, ethyl, propyl, isopropyl, n-butyl, isobutyl, s-butyl and t-butyl. $r^3$ and $r^5$ may join to form a bond. Of them, $r^1$ to $r^9$ are more preferably hydrogen, methyl or ethyl.

More preferred hetero rings represented by Q include isooxazolyl groups such as isooxazol-3-yl, 4-methyl-isooxazol-3-yl, 5-methyl-isooxazol-3-yl, 4,5-dimethylisooxazol-3-yl, 4-ethyl-isooxazol-3-yl, 5-ethyl-isooxazol-3-yl, 4,5-diethylisooxazol-3-yl, isooxazol-5-yl, 3-methyl-isooxazol-5-yl, 4-methyl-isooxazol-5-yl, 3,4-dimethylisooxazol-5-yl, 3-ethyl-isooxazol-5-yl, 4-ethyl-isooxazol-5-yl and 3,4-diethylisooxazol-5-yl; isooxazoline groups such as isooxazolin-3-yl, 4-methyl-isooxazolin-3-yl, 5-methyl-isooxazolin-3-yl, 4-ethyl-isooxazolin-3-yl and 5-ethyl-isooxazolin-3-yl; and pyrazolyl groups such as pyrazol-3-yl, 1-methylpyrazol-3-yl, 1-ethylpyrazol-3-yl, 1-propylpyrazol-3-yl and 1,5-dimethylpyrazol-3-yl.

The compounds of the present invention may be produced according to the following processes:

(Process 1) Process for the preparation of a thiophenol compound substituted with a hetero ring represented by Formula (1)

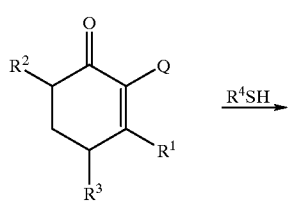

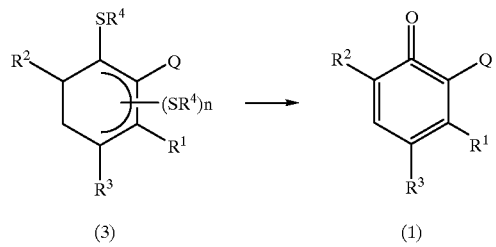

(wherein $R^1$ to $R^4$, n and Q are as defined above).

The process is to obtain a compound of (1) by S-alkylating a compound of Formula (2) to give an intermediate (3), followed by a dehydrogenation reaction.

The S-alkylation reaction is carried out by dissolving a cyclohexenone compound substituted with a hetero ring (2) in an appropriate inert solvent, and reacting it with 1 to 5 equivalents of alkane thiol at temperature between $-20°$ C. and the boiling point of the solvent used. This reaction may proceed more smoothly by adding 0.01 to 2 equivalents of a compound including acids such as p-toluenesulfonic acid and sulfuric acid or Lewis acids such as aluminum chloride, zinc chloride and boron trifluoride etherate.

Solvents that may be used for this reaction include alcohols such as methanol and ethanol; halogenated hydrocarbons such as methylene chloride, chloroform and chlorobenzene; hydrocarbons such as n-hexane, benzene and toluene; and ethers such as tetrahydrofuran (THF) and dimethoxyethane.

The next dehydrogenation reaction is carried out by dissolving a cyclohexene derivative or cyclohexane derivative (3) in an appropriate solvent and dehyrogenating it in the presence of a dehydrogenating agent at temperature between $-10°$ C. and the boiling point of the solvent used.

Dehydrogenating agents used for the dehydrogenation reaction include quinones such as 2,3-dichloro-5,6-dicyano-1,4-benzoquinone (DDQ) and tetrachloro-1,4-benzoquinone; halogens such as chlorine and bromine; halogenated imides such as N-chlorosuccinimide and N-bromosuccinimide; oxidizing agents such as manganese dioxide and nickel peroxide, or sulfur and sulfur coexisting with dimethyl sulfoxide.

Proper solvents used include hydrocarbons such as benzene, toluene and mesitylene; halogenated hydrocarbons such as chloroform and chlorobenzene; sulfur containing compounds such as dimethyl sulfoxide and sulfolane; alcohols such as ethanol and ethylene glycol; ethers such as ether and THF; and acetic acid.

(Process 2) Process for the preparation of a cyclohexenone compound of Formula (2) from an enol lactone compound represented by Formula (5)

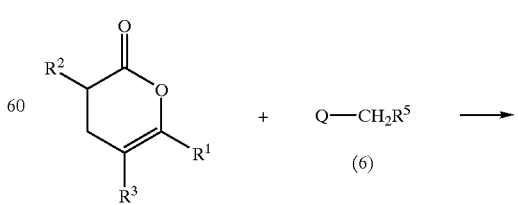

-continued

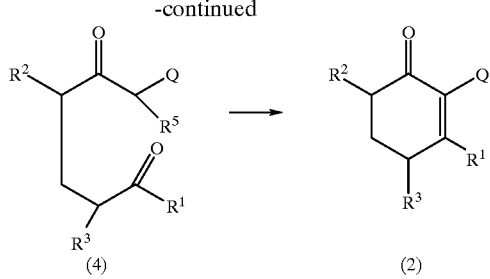

(wherein $R^1$ to $R^3$, $R^5$ and Q are as defined above.)

A compound (2) of the present invention can be produced by that an enol lactone (5) and a hetero-ring derivative (6) are reacted in an inert solvent at temperature between 0° C. and the boiling point of the solvent used in the presence of a base, and the obtained compound (4) is treated with a base or an acid for a cyclization reaction with the elimination of $R^5$ group.

When a hetero-ring derivative (6) where $R^5$ is hydrogen is used, a compound (2) of the present invention can be produced without isolating a compound (4) by that the derivative (6) is reacted with a strong base such as n-butyl lithium, lithium diisopropylamide or potassium t-butoxide at temperature between −78° C. and the boiling point of the solvent used, followed by the reaction with an enol lactone (5). This reaction may finish more smoothly and in a shorter time when an additive such as tetramethylethylenediamine (TMEDA) or hexamethylphosphortriamide (HMPA) is present in the reaction system.

Solvents used in the above reaction to obtain the compound (4) include hydrocarbons such as n-hexane, benzene and toluene; halogenated hydrocarbons such as dichloromethane, chloroform and monochlorobenzene; ethers such as THF, diethyl ether and dimethoxyethane; alcohols such as t-butanol and isopentyl alcohol; amides such as DMF, N-methylpyrolidone and N,N-dimethylimidazolyl-2-one (DMI); and sulfur-containing ethers such as DMSO; and nitriles such as acetonitrile. They may be used alone or as a mixed solvent of two or more.

Bases used in the reaction include alkali metal hydroxides such as sodium hydroxide and potassium hydroxide; alkaline earth metal hydroxides such as calcium hydroxide and magnesium hydroxide; alkali metal carbonates such as potassium carbonate and cecium carbonate; alkaline earth metal carbonates such as calcium carbonate and magnesium carbonate; metal alcolates such as sodium methylate and potassium t-butoxide; metal hydrides such as sodium hydride; and organic bases such as triethylamine, diisopropylethylamine, pyridine, 1,8-diazabicyclo[5.4.0]undec-7-ene (DBU). A preferred amount of a base used is 0.1 to 5 times in mole to the reaction substrate.

The reaction may finish more smoothly and in a shorter time by adding quaternary ammonium salts such as triethylbenzyl ammonium chloride or crown ethers such as 18-crown-6.

For the latter reaction to give the compound (2), the solvents and bases exemplified for the first reaction may be preferably used.

For example, when a compound (6) where $R^5$ is an alkylcarbonyl group is used, the aforementioned bases are used. It is preferable to carry out the reaction in the presence of a base including amines such as triethylamine and pyridine and metal alcolates such as sodium methylate and potassium t-butoxide, so that a cyclization reaction proceeds simultaneously with deacylation to give a compound (2) of the present invention. This reaction is favorably carried out at temperature between 0° C. and the boiling point of the solvent used.

When a compound (6) where $R^5$ is a cyano or alkoxycarbonyl group is used, it is hydrolyzed with an acid such as hydrochloric acid or sulfuric acid or a base exemplified for the first reaction, and then a decarboxylation reaction followed by a cyclization reaction gives a compound (2) of this invention.

Enol lactones represented by Formula (5) may be synthesized by, for example, a reaction between a ketocarboxylic acid and thionyl chloride in benzene as described in J. Org. Chem. 50, 4105–4107 (1985), or a reaction between an acid chloride of ketocarboxylic acid and sodium hydrogen carbonate as described in J. Org. Chem. 55, 157–172 (1990), or the like.

The compounds and intermediates and others of the present invention may be obtained with ordinary post-treatments after the completion of the reactions.

The structures of the compounds, intermediates and others of the present invetnion were determined by such means as IR, NMR and MS.

BEST FORM TO IMPLEMENT THE INVENTION

The present invention is further described in detail with Examples and Reference Examples.

EXAMPLE 1

Preparation of 3-methyl-5-(2-methyl-6-methylthiophenyl) isoxazole [Compound (1)-1]

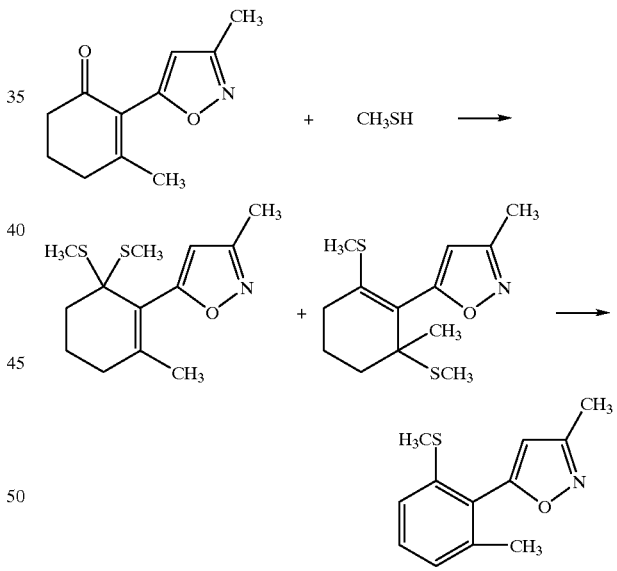

4.0 g (20.9 mmol) of 3-methyl-2-(3-methylisooxazol-5-yl)-2-cyclohexen-1-one was dissolved in 60 ml of chloroform, and 0.84 g (6.3 mmol) of aluminum chloride was added. The resulting solution was cooled down to −5° C. and 3.0 g (62.7 mmol) of methanethiol was blown into it, followed by stirring for a whole day and night at room temperature. The reaction solution was poured into 2N hydrochloric acid. The chloroform layer was washed with water, dehydrated over anhydrous magnesium sulfate and concentrated to give 6.1 g of a mixture of 6,6-dimethylthio-2-methyl-1-(3-methylisooxazol-5-yl)-1-cyclohexene [Compound (3)-1] and 2,6-dimethylthio-2-methyl-1-(3-methylisooxazol-5-yl)-6-cyclohexene [Compound (3)-2].

NMR data of Compound (3)-1:

$^1$H-NMR (CDCl$_3$, δ ppm): 1.57 (s, 3H), 1.90–2.25 (m, 6H), 1.98 (s, 6H), 2.31 (s, 3H), 6.11 (s, 1H).

NMR data of Compound (3)-2:

$^1$H-NMR(CDCl$_3$, δ ppm): 1.31 (s, 3H), 1.80 (m, 2H), 1.90–2.20 (m, 2H), 1.99 (s, 3H), 2.19 (s, 3H), 2.34 (s, 3H), 2.42 (m, 2H), 6.12 (s, 1H).

6.1 g of the obtained mixture of the dimethylthio compounds was dissolved in 100 ml of chloroform, into which a solution of 4.0 g (25.0 mmol) of bromine in 15 ml of chloroform was dropped with stirring at room temperature. After the completion of the dropping, the solution was further stirred for 3 hours at room temperature. The reaction solution was washed with an aqueous solution of sodium thiosulfate and then with water, dried over anhydrous magnesium sulfate and concentrated. The obtained crude product was purified on silica gel column chromatography to give 3.7 g of the title compound as a colorless liquid. Boiling point: 121–122° C./0.2 mmHg.

EXAMPLE 2

Preparation of 3-methyl-5-(2-methyl-6-methylthiophenyl) isoxazole [Compound (1)-1]

0.50 g of a mixture of the dimethylthio compounds obtained in the same way as that in Example 1 and 0.15 g of dimethyl sulfoxide were dissolved in 5 ml of xylene, and 0.065 g of sulfur was added. The resulting solution was heated at reflux for 18 hours. After cooling, the reaction solution was concentrated under reduced pressure. The obtained crude product was purified on silica gel column chromatography to give 0.21 g of the title compound as a colorless liquid.

EXAMPLE 3

Preparation of 3-methyl-5-(2-methyl-6-methylthiophenyl) isoxazole [Compound (1)-1]

0.40 g of a mixture of the dimethylthio compounds obtained in the same way as that in Example 1 was dissolved in 7 ml of xylene, and 0.55 g of tetrachloro-1,4-benzoquinone was added. The resulting solution was heated at reflux for 2 hours. After cooling down, the reaction solution was washed with a 1N aqueous solution of sodium hydroxide. The organic layer was washed with saturated salt water and dried over anhydrous magnesium sulfate. The solvent was removed by distillation under reduced pressure to give 0.24 g (purity: 92%) of the title compound as a liquid.

EXAMPLE 4

Preparation of ethyl 2-methyl-3-(3-methylisooxazol-5-yl)4-methylthiobenzoate [Compound (1)-2]

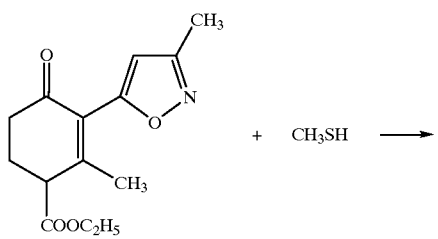

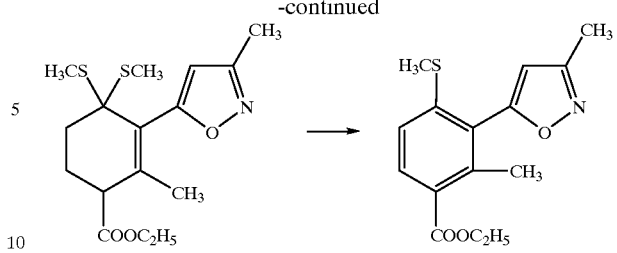

1.0 g (purity: 61.5%) of 4-ethoxycarbonyl-2-(3-methylisooxazol-5-yl)-3-methyl-2-cyclohexen-1-one was dissolved in 20 ml of chloroform, and 0.09 g of aluminum chloride was added. The resulting solution was cooled to below 0° C. and 60 ml of methanethiol was introduced into it using a float meter. After returning to room temperature, the solution was stirred for 15 hours. The reaction solution was poured into cold water and 5 ml of 2N hydrochloric acid was added to separate. The chloroform layer was washed with water, dehydrated over anhydrous magnesium sulfate and concentrated. The obtained crude product was purified on silica gel column chromatography to give 0.56 g of ethyl 4,4-dimethylthio-2-methyl-3-(3-methylisooxazol-5-yl)-2-cyclohexene carboxylate [Compound (3)-3] as a light yellow liquid.

NMR data of Compound (3)-3:

$^1$H-NMR (CDCl$_3$, δ ppm): 1.30 (t, 3H), 1.63 (s, 3H), 1.80 (m, 2H), 2.04 (s, 3H), 2.07 (s, 3H), 2.05–2.15 (m, 2H), 2.25–2.35 (m, 2H), 2.34 (s, 3H), 3.14 (m, 1H), 4.21 (q, 2H), 6.19 (s, 1H).

0.55 g of ethyl-4,4-dimethylthio-2-methyl-3-(3-methylisooxazol-5-yl)-2-cyclohexene carboxylate obtained above was dissolved in 10 ml of chloroform, into which a solution of 0.28 g of bromine in 1 ml of chloroform was dropped at room temperature. Gas generation was observed simultaneously with dropping. After the completion of the dropping, the solution was further stirred for an hour at room temperature. The reaction solution was poured into cold water and extracted with chloroform. The extract chloroform layer was washed with water, dehydrated over anhydrous magnesium sulfate and concentrated. The obtained crude product was purified on silica gel column chromatography to give 0.37 g of the title compound as white crystals. Melting point: 72–74° C.

EXAMPLE 5

Preparation of 2-(3-methylisooxazol-5-yl)-3-methyl-2-cyclohexen-1-one [Compound (2)-1]

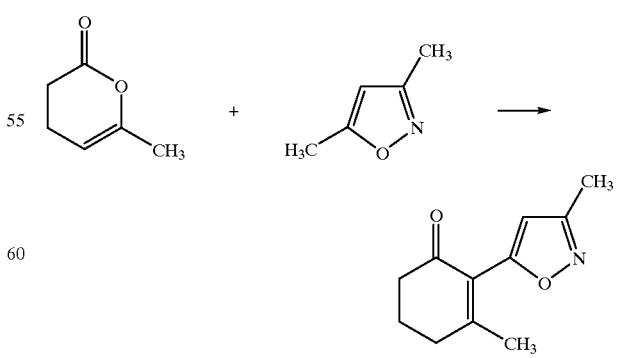

4.75 g of TMEDA was dissolved in 10 ml of THF, and 3.3 g of 3,5-dimethylisoxazole was added. The resulting solution was cooled to −78° C. in a dry ice-acetone bath, and 26 ml of an n-hexane solution of n-butyl lithium (1.6M solution) was dropped into it. They were reacted at the same temperature for 30 minutes, and then, at −78° C., a solution of 1.90 g of 3,4-dihydro-6-methyl-2H-pyran-2-one and 5 ml of DMSO in 10 ml of THF was dropped. The resulting solution was stirred at the same temperature for 2 hours. The dry ice-acetone bath was taken away. After gradually returning to room temperature, the solution was stirred for 15 hours. The reaction solution was poured into dilute hydrochloric acid-ice and extracted with ethyl acetate. The organic layer was washed with water and then with saturated salt water, and dried over anhydrous magnesium sulfate. The solvent was concentrated under reduced pressure. The obtained residue was purified on silica gel column chromatography to give 1.10 g of the title compound as white crystals. Melting point: 104–105° C.

EXAMPLE 6

Preparation of 3-methylisooxazol-5-yl-2,4,8-nonanetrione [Compound (3)-1]

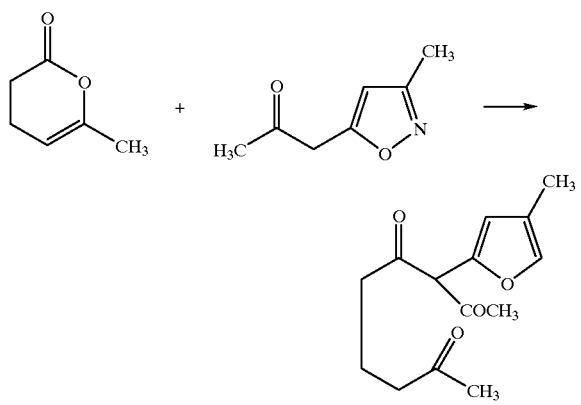

1.39 g of 5-acetonyl-3-methylisoxazole, 1.68 g of 3,4-dihydro-6-methyl-2H-pyran-2-one and 3.42 g of cecium carbonate were added to 20 ml of acetonitrile to heat at reflux for 3 hours. After returning to room temperatrure, the reaction solution was poured into 100 ml of ice water with hydrochloric acid added, and extracted with ethyl acetate. The organic layer was washed with water and then with saturated salt water, and dried over magnesium sulfate. The solvent was concentrated under reduced pressure. The obtained crude product was purified on silica gel column chromatography to give 2.03 g of the title compound as a colorless viscous liquid.

$^1$H-NMR (CDCl$_3$, δ ppm): 1.83 (m, 2H), 2.01 (s, 3H), 2.10 (s, 3H), 2.28 (t, 2H), 2.33 (s, 3H), 2.44 (t, 2H), 6.06 (s, 1H), 16.98 (s, 1H).

EXAMPLE 7

Preparation of 2-(3-methylisooxazol-5-yl)-3-methyl-2-cyclohexen-1-one [Compound (2)-1]

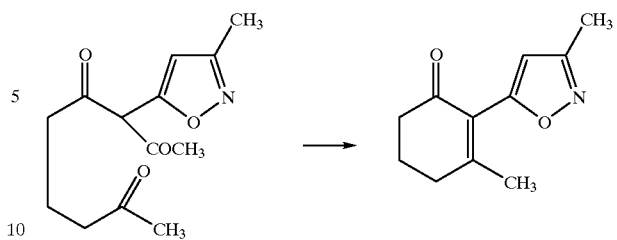

1.2 g of 3-methylisooxazol-5-yl-2,4,8-nonanetrione obtained in Example 6 was dissolved in 15 ml of ethanol, and 0.53 g of triethylamine was added to it to stir at reflux for 8 hours. After cooling, the reaction solution was poured into ice water, acidified with hydrochloric acid and extracted with ethyl acetate. The ethyl-acetate layer was washed with water, dehydrated over anhydrous magnesium sulfate, and concentrated. The obtained residue was purified on silica gel column chromatography to give 0.36 g of the title compound as white crystals. Melting point: 104–105° C.

EXAMPLE 8

Preparation of ethyl 2-acetyl-5,7-dioxo-6-(3-methylisooxazol-5-yl)octanoate [Compound (3)-2]

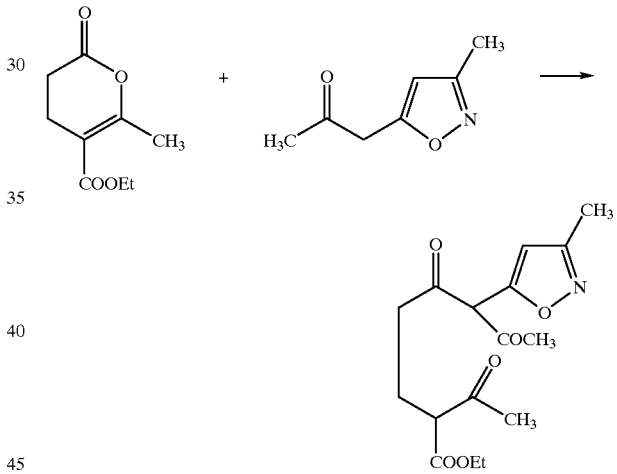

16.44 g of 5-acetonyl-3-methylisoxazole was dissolved in 300 ml of acetonitrile, and a solution of 28.30 g of 5-ethoxycarbonyl-3,4-dihydro-6-methyl-2H-2-one in 30 ml of acetonitrile and 40.47 g of cesium carbonate were added to it to stir for 2 hours at room temperature. Water was added to the reaction solution. The resulting solution was acidified with 2N hydrochloric acid and extracted with ether. The aqueous layer was further extracted with ethyl acetate. The obtained organic layers were combined and dried over anhydrous magnesium sulfate. The solvents were removed by distillation. The residue was purified on silica gel column chromatography to give 29.80 g of the title compound as a light yellow liquid.

$^1$H-NMR (CDCl$_3$, δ ppm): 1.24 (t, 3H), 2.03 (s, 3H), 2.13 (m, 2H), 2.24 (m, 4H), 2.31 (s, 3H), 2.34 (t, 1H), 4.18 (q, 2H), 6.07 (s, 1H), 16.91 (s, 11).

EXAMPLE 9

Preparation of 4-ethoxycarbony-2-(3-methylisooxazol-5-yl)-3-methyl-2-cyclohexen-1-one [Compound (2)-2]

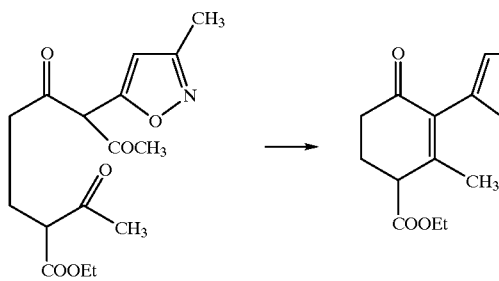

0.85 g of the obtained ethyl 2-acetyl-5,7-dioxo-6-(3-methylisooxazol-5-yl)octanoate was dissolved in 5 ml of methanol and 0.32 g of triethylamine was added. The resulting solution was stirred at room temperature for 2 hours and then heated at reflux for 3 hours. After cooling, water was added to the reaction solution to extract with ethyl acetate. The organic layer was washed with saturated salt water and dried over anhydrous magnesium sulfate. The solvent was removed by distillation. The obtained residue was purified on silica gel column chromatography to give 0.27 g of the title compound as a colorless liquid.

$^1$H-NMR (CDCl$_3$, δppm): 1.31 (t, 3H), 2.13 (s, 3H), 2.33 (s, 31H), 2.4 (m, 2H), 2.6 (m, 2H), 3.50 (m, 1H), 4.25 (q, 2H), 6.30 (s, 1H).

REFERENCE EXAMPLE 1
Preparation of 5-acetonyl-3-methylisoxazole

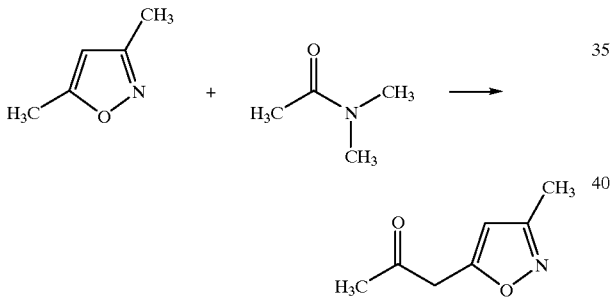

Into a 2 L flask filled with nitrogen were placed 1000 ml of anhydrous THF and 500 ml of a 1.6M n-hexane solution of n-butyl lithium. The flask was placed in a dry ice-acetone bath to set the inside temperature to −70° C., and 68.0 g of 3,5-dimethylisoxazole was slowly dropped in the flask. After the resulting solution was stirred for 30 minutes at the same temperature, a solution of 120.0 g of dimethylacetamide in 300 ml of THF was slowly dropped. After the completion of the dropping, the solution was further stirred for an hour at −60° C. to −65° C. The reaction solution was poured into 1 L of ice water acidified with hydrochloric acid. The organic layer was separated. The aqueous layer was further extracted with ethyl acetate. The obtained organic layers were combined and concentrated under reduced pressure. The obtained concentrate was dissolved in 500 ml of ethyl acetate, washed with water and then with saturated salt water, and dried over anhydrous magnesium sulfate. The solvent was removed by distillation. The residue was purified by distillation under reduced pressure to give 68.5 g of the title compound as a colorless liquid. Boiling point: 85° C./1.0 mmHg.

REFERENCE EXAMPLE 2
Preparation of 5-acetonyl-3-methylisoxazole

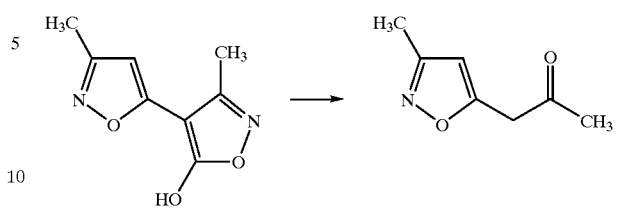

9.70 g of 5-hydroxy-3-methyl-4-(3-methylisooxazol-5-yl)isoxazole was added to 18 ml of acetic acid and 30 ml of methanol, and was heated to 60° C. to dissolve. To the resulting solution was added 3.20 g of electrolytic iron powder to stir for an hour at 60° C. 20 ml of 3N hydrochloric acid was further added to the reaction solution to stir for 20 minutes at 60° C. The reaction mixture was cooled to room temperature and water was added. The mixture was extracted with ethyl acetate. The organic layer was washed with saturated salt water, dried over anhydrous magnesium sulfate and concentrated to give 6.00 g of the title compound as a reddish brown liquid.

REFERENCE EXAMPLE 3
Preparation of 5-acetonyl-3-methylisoxazole

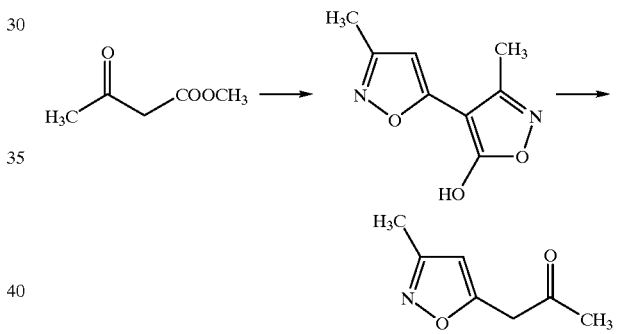

208 g of a 50% aqueous hydroxylamine solution and 91 ml of 28% aqueous ammonia were added to 350 ml of water, into which 348 g of methyl acetoacetate was dropped over 50 minutes at temperature below 15° C. After the completion of the dropping, the reaction solution returned to room temperature and stood undisturbed for 6 days to give 900 ml of an aqueous solution of crude ammonium salt of 5-hydroxy-3-methyl-4-(3-methylisooxazol-5-yl)isoxazole.

Then, 600 ml of 6N hydrochloric acid and 300 ml of toluene were mixed to heat to 80° C. and 39.0 g of electrolytic iron powder was added, and 300 ml of the aqueous solution of crude ammonium salt of 5-hydroxy-3-methyl-4-(3-methylisooxazol-5-yl)isoxazole obtained above was dropped over 30 minutes at 80° C. The solution was firter stirred for 30 minutes at the same temperature. The reaction solution was cooled to room temperature. The toluene layer was separated. The aqueous layer was fuirther extracted with ethyl acetate. The organic layers were combined, washed with saturated salt water and then with aqueous sodium bicarbonate, and dried over anhydrous magnesium sulfate. The solvents were removed by distillation under reduced pressure. The residue was distilled under reduced pressure to give 28.0 g of the title compound as a light yellow liquid. Boiling point: 98° C./2 mmHg.

REFERENCE EXAMPLE 4

Preparation of 5-ethoxycarbonyl-3,4-dihydro-6-methyl-2H-pyran-2-one

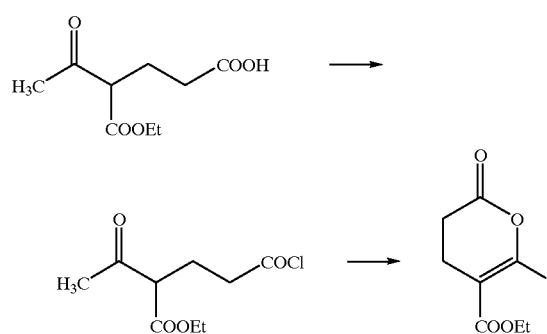

55.2 g of monoethyl 2-acetylglutarate was dissolved in 500 ml of methylene chloride, and 52.06 g of oxalyl chloride and 5 drops of DMF were added at 0° C. They were reacted for 2 hours at room temperature. 500 ml of methylene chloride was added to the obtained acid-chloride solution, and, at temperature below 10° C., 33.12 g of triethylamine was dropped. They were reacted for an hour at room temperature. The reaction solution was washed with water, with an aqueous solution of sodium hydrogen carbonate and then with saturated salt water, and dried over anhydrous magnesium sulfate. The solvent was removed by distillation. The obtained residue was purified by distillation under reduced pressure to give 29.30 g of the title compound as a colorless liquid. Boiling point: 130–150° C./17 mmHg.

Representative examples of the compounds of Formula (1) of the present invention, including those in the above examples, are shown in Table 1, those of Formula (2) in Table 2, and those of Formula (4) in Table 3.

TABLE 1

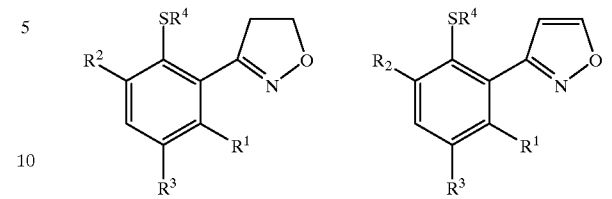

| $R^1$ | $R^2$ | $R^3$ | $R^4$ | $R^1$ | $R^2$ | $R^3$ | $R^4$ |
|---|---|---|---|---|---|---|---|
| $CH_3$ | H | H | $CH_3$ | $CH_3$ | $CH_3$ | $COCH_3$ | $CH_3$ |
| $CH_3$ | $CH_3$ | H | $CH_3$ | $CH_3$ | $C_2H_5$ | $COCH_3$ | $CH_3$ |
| $CH_3$ | $C_2H_5$ | H | $CH_3$ | $CH_3$ | H | $COC_2H_5$ | $CH_3$ |
| $CH_3$ | H | $COOCH_3$ | $CH_3$ | $CH_3$ | $CH_3$ | $COC_2H_5$ | $CH_3$ |
| $CH_3$ | $CH_3$ | $COOCH_3$ | $CH_3$ | $CH_3$ | $C_2H_5$ | $COC_2H_5$ | $CH_3$ |
| $CH_3$ | $C_2H_5$ | $COOCH_3$ | $CH_3$ | $CH_3$ | H | CN | $CH_3$ |
| $CH_3$ | H | $COOC_2H_5$ | $CH_3$ | $CH_3$ | $CH_3$ | CN | $CH_3$ |
| $CH_3$ | $CH_3$ | $COOC_2H_5$ | $CH_3$ | $CH_3$ | $C_2H_5$ | CN | $CH_3$ |
| $CH_3$ | $C_2H_5$ | $COOC_2H_5$ | $CH_3$ | $CH_3$ | H | $CONH_2$ | $CH_3$ |
| $CH_3$ | H | $COCH_3$ | $CH_3$ | $CH_3$ | $CH_3$ | $CONH_2$ | $CH_3$ |
| $CH_3$ | $C_2H_5$ | $CONH_2$ | $CH_3$ | $C_2H_5$ | H | $COOCH_3$ | $CH_3$ |
| $CH_3$ | H | H | $C_2H_5$ | $C_2H_5$ | $CH_3$ | $COOCH_3$ | $CH_3$ |
| $CH_3$ | $CH_3$ | H | $C_2H_5$ | $C_2H_5$ | $C_2H_5$ | $COOCH_3$ | $CH_3$ |
| $CH_3$ | $C_2H_5$ | H | $C_2H_5$ | $C_2H_5$ | H | $COOC_2H_5$ | $CH_3$ |
| $CH_3$ | H | $COOCH_3$ | $C_2H_5$ | $C_2H_5$ | $CH_3$ | $COOC_2H_5$ | $CH_3$ |
| $CH_3$ | $CH_3$ | $COOCH_3$ | $C_2H_5$ | $C_2H_5$ | $C_2H_5$ | $COOC_2H_5$ | $CH_3$ |
| $CH_3$ | $C_2H_5$ | $COOCH_3$ | $C_2H_5$ | $C_2H_5$ | H | $COCH_3$ | $CH_3$ |
| $CH_3$ | H | $COOC_2H_5$ | $C_2H_5$ | $C_2H_5$ | $CH_3$ | $COCH_3$ | $CH_3$ |
| $CH_3$ | $CH_3$ | $COOC_2H_5$ | $C_2H_5$ | $C_2H_5$ | $C_2H_5$ | $COCH_3$ | $CH_3$ |
| $CH_3$ | $C_2H_5$ | $COOC_2H_5$ | $C_2H_5$ | $C_2H_5$ | H | $COC_2H_5$ | $CH_3$ |
| $CH_3$ | H | $COCH_3$ | $C_2H_5$ | $C_2H_5$ | $CH_3$ | $COC_2H_5$ | $CH_3$ |
| $CH_3$ | $CH_3$ | $COCH_3$ | $C_2H_5$ | $C_2H_5$ | $C_2H_5$ | $COC_2H_5$ | $CH_3$ |
| $CH_3$ | $C_2H_5$ | $COCH_3$ | $C_2H_5$ | $C_2H_5$ | H | CN | $CH_3$ |
| $CH_3$ | H | $COC_2H_5$ | $C_2H_5$ | $C_2H_5$ | $CH_3$ | CN | $CH_3$ |
| $CH_3$ | $CH_3$ | $COC_2H_5$ | $C_2H_5$ | $C_2H_5$ | $C_2H_5$ | CN | $CH_3$ |
| $CH_3$ | $C_2H_5$ | $COC_2H_5$ | $C_2H_5$ | $C_2H_5$ | H | $CONH_2$ | $CH_3$ |
| $CH_3$ | H | CN | $C_2H_5$ | $C_2H_5$ | $CH_3$ | $CONH_2$ | $CH_3$ |
| $CH_3$ | $CH_3$ | CN | $C_2H_5$ | $C_2H_5$ | $C_2H_5$ | $CONH_2$ | $CH_3$ |
| $CH_3$ | $C_2H_5$ | CN | $C_2H_5$ | $C_2H_5$ | H | H | $CH_3$ |
| $CH_3$ | H | $CONH_2$ | $C_2H_5$ | $C_2H_5$ | $CH_3$ | H | $CH_3$ |
| $CH_3$ | $CH_3$ | $CONH_2$ | $C_2H_5$ | $C_2H_5$ | $C_2H_5$ | H | $CH_3$ |
| $CH_3$ | $C_2H_5$ | $CONH_2$ | $C_2H_5$ | $C_2H_5$ | H | $COOCH_3$ | $CH_3$ |
| $C_2H_5$ | H | H | $CH_3$ | $C_2H_5$ | $CH_3$ | $COOCH_3$ | $CH_3$ |
| $C_2H_5$ | $CH_3$ | H | $CH_3$ | $C_2H_5$ | $C_2H_5$ | $COOCH_3$ | $CH_3$ |
| $C_2H_5$ | $C_2H_5$ | H | $CH_3$ | $C_2H_5$ | H | $COOC_2H_5$ | $CH_3$ |
| $C_2H_5$ | CH | $COOC_2H_5$ | $CH_3$ | $C_2H_5$ | $C_2H_5$ | $COC_2H_5$ | $C_2H_5$ |
| $C_2H_5$ | $C_2H_5$ | $COOC_2H_5$ | $CH_3$ | $C_2H_5$ | H | CN | $C_2H_5$ |
| $C_2H_5$ | H | $COCH_3$ | $C_2H_5$ | $C_2H_5$ | $CH_3$ | CN | $C_2H_5$ |
| $C_2H_5$ | $CH_3$ | $COCH_3$ | $C_2H_5$ | $C_2H_5$ | $C_2H_5$ | CN | $C_2H_5$ |
| $C_2H_5$ | $C_2H_5$ | $COCH_3$ | $C_2H_5$ | $C_2H_5$ | H | $CONH_2$ | $C_2H_5$ |
| $C_2H_5$ | H | $COC_2H_5$ | $C_2H_5$ | $C_2H_5$ | $CH_3$ | $CONH_2$ | $C_2H_5$ |
| $C_2H_5$ | $CH_3$ | $COC_2H_5$ | $C_2H_5$ | $C_2H_5$ | $C_2H_5$ | $CONH_2$ | $C_2H_5$ |

TABLE 2

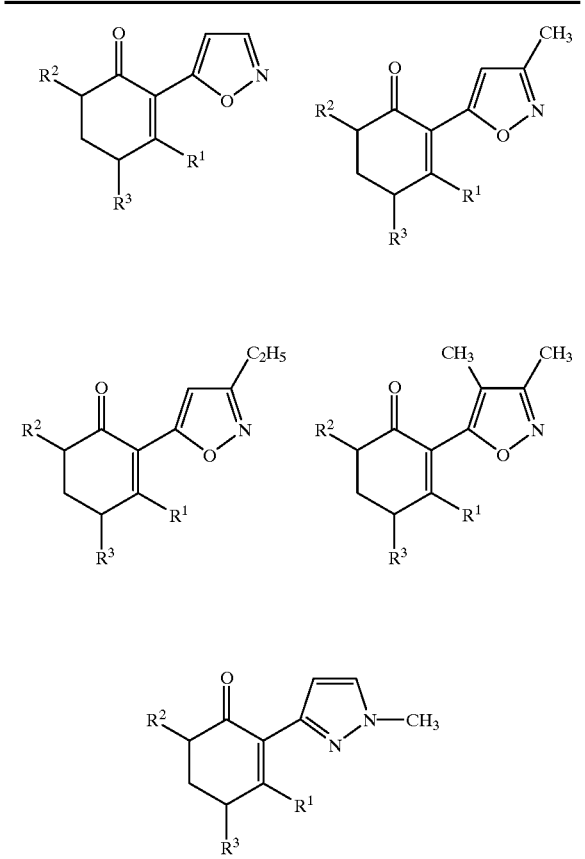

TABLE 2-continued

| R¹ | R² | R³ | R¹ | R² | R³ |
|---|---|---|---|---|---|
| $CH_3$ | H | H | $C_2H_5$ | H | H |
| $CH_3$ | $CH_3$ | H | $C_2H_5$ | $CH_3$ | H |
| $CH_3$ | $C_2H_5$ | H | $C_2H_5$ | $C_2H_5$ | H |
| $CH_3$ | H | $COOCH_3$ | $C_2H_5$ | H | $COOCH_3$ |
| $CH_3$ | $CH_3$ | $COOCH_3$ | $C_2H_5$ | $CH_3$ | $COOCH_3$ |
| $CH_3$ | $C_2H_5$ | $COOCH_3$ | $C_2H_5$ | $C_2H_5$ | $COOCH_3$ |
| $CH_3$ | H | $COOC_2H_5$ | $C_2H_5$ | H | $COOC_2H_5$ |
| $CH_3$ | $CH_3$ | $COOC_2H_5$ | $C_2H_5$ | $CH_3$ | $COOC_2H_5$ |
| $CH_3$ | $C_2H_5$ | $COOC_2H_5$ | $C_2H_5$ | $C_2H_5$ | $COOC_2H_5$ |
| $CH_3$ | H | $COCH_3$ | $C_2H_5$ | H | $COCH_3$ |
| $CH_3$ | $CH_3$ | $COCH_3$ | $C_2H_5$ | $CH_3$ | $COCH_3$ |
| $CH_3$ | $C_2H_5$ | $COCH_3$ | $C_2H_5$ | $C_2H_5$ | $COCH_3$ |
| $CH_3$ | H | $COC_2H_5$ | $C_2H_5$ | H | $COC_2H_5$ |
| $CH_3$ | $CH_3$ | $COC_2H_5$ | $C_2H_5$ | $CH_3$ | $COC_2H_5$ |
| $CH_3$ | $C_2H_5$ | $COC_2H_5$ | $C_2H_5$ | $C_2H_5$ | $COC_2H_5$ |
| $CH_3$ | H | CN | $C_2H_5$ | H | CN |
| $CH_3$ | $CH_3$ | CN | $C_2H_5$ | $CH_3$ | CN |
| $CH_3$ | $C_2H_5$ | CN | $C_2H_5$ | $C_2H_5$ | CN |
| $CH_3$ | H | $CONH_2$ | $C_2H_5$ | H | $CONH_2$ |
| $CH_3$ | $CH_3$ | $CONH_2$ | $C_2H_5$ | $CH_3$ | $CONH_2$ |
| $CH_3$ | $C_2H_5$ | $CONH_2$ | $C_2H_5$ | $C_2H_5$ | $CONH_2$ |

TABLE 3

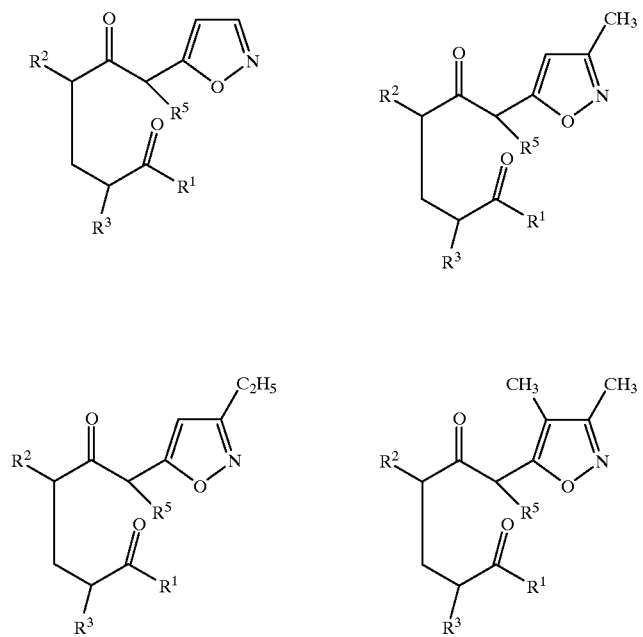

TABLE 3-continued

| R¹ | R² | R³ | R⁵ | R¹ | R² | R³ | R⁵ |
|---|---|---|---|---|---|---|---|
| CH₃ | H | H | COCH₃ | C₂H₅ | H | H | COCH₃ |
| CH₃ | CH₃ | H | COCH₃ | C₂H₅ | CH₃ | H | COCH₃ |
| CH₃ | C₂H₅ | H | COCH₃ | C₂H₅ | C₂H₅ | H | COCH₃ |
| CH₃ | H | COOCH₃ | COCH₃ | C₂H₅ | H | COOCH₃ | COCH₃ |
| CH₃ | CH₃ | COOCH₃ | COCH₃ | C₂H₅ | CH₃ | COOCH₃ | COCH₃ |
| CH₃ | C₂H₅ | COOCH₃ | COCH₃ | C₂H₅ | C₂H₅ | COOCH₃ | COCH₃ |
| CH₃ | H | COOC₂H₅ | COCH₃ | C₂H₅ | H | COOC₂H₅ | COCH₃ |
| CH₃ | CH₃ | COOC₂H₅ | COCH₃ | C₂H₅ | CH₃ | COOC₂H₅ | COCH₃ |
| CH₃ | C₂H₅ | COOC₂H₅ | COCH₃ | C₂H₅ | C₂H₅ | COOC₂H₅ | COCH₃ |
| CH₃ | H | COCH₃ | COCH₃ | C₂H₅ | H | COCH₃ | COCH₃ |
| CH₃ | CH₃ | COCH₃ | COCH₃ | C₂H₅ | CH₃ | COCH₃ | COCH₃ |
| CH₃ | C₂H₅ | COCH₃ | COCH₃ | C₂H₅ | C₂H₅ | COCH₃ | COCH₃ |
| CH₃ | H | COC₂H₅ | COCH₃ | C₂H₅ | H | COC₂H₅ | COCH₃ |
| CH₃ | CH₃ | COC₂H₅ | COCH₃ | C₂H₅ | CH₃ | COC₂H₅ | COCH₃ |
| CH₃ | C₂H₅ | COC₂H₅ | COCH₃ | C₂H₅ | C₂H₅ | COC₂H₅ | COCH₃ |
| CH₃ | H | CN | COCH₃ | C₂H₅ | H | CN | COCH₃ |
| CH₃ | CH₃ | CN | COCH₃ | C₂H₅ | CH₃ | CN | COCH₃ |
| CH₃ | C₂H₅ | CN | COCH₃ | C₂H₅ | C₂H₅ | CN | COCH₃ |
| CH₃ | H | CONH₂ | COCH₃ | C₂H₅ | H | CONH₂ | COCH₃ |
| CH₃ | CH₃ | CONH₂ | COCH₃ | C₂H₅ | CH₃ | CONH₂ | COCH₃ |
| CH₃ | C₂H₅ | CONH₂ | COCH₃ | C₂H₅ | C₂H₅ | CONH₂ | COCH₃ |
| CH₃ | H | H | COC₂H₅ | C₂H₅ | H | H | COCH₃ |
| CH₃ | CH₃ | H | COC₂H₅ | C₂H₅ | CH₃ | H | COCH₃ |
| CH₃ | C₂H₅ | H | COC₂H₅ | C₂H₅ | C₂H₅ | H | COCH₃ |
| CH₃ | H | COOCH₃ | COC₂H₅ | C₂H₅ | H | COOCH₃ | COCH₃ |
| CH₃ | CH₃ | COOCH₃ | COC₂H₅ | C₂H₅ | CH₃ | COOCH₃ | COCH₃ |
| CH₃ | C₂H₅ | COOCH₃ | COC₂H₅ | C₂H₅ | C₂H₅ | COOCH₃ | COCH₃ |
| CH₃ | H | COOC₂H₅ | COC₂H₅ | C₂H₅ | H | COOC₂H₅ | COC₂H₅ |
| CH₃ | CH₃ | COOC₂H₅ | COC₂H₅ | C₂H₅ | CH₃ | COOC₂H₅ | COC₂H₅ |
| CH₃ | C₂H₅ | COOC₂H₅ | COC₂H₅ | C₂H₅ | C₂H₅ | COOC₂H₅ | COC₂H₅ |
| CH₃ | H | COCH₃ | COC₂H₅ | C₂H₅ | H | COCH₃ | COC₂H₅ |
| CH₃ | CH₃ | COCH₃ | COC₂H₅ | C₂H₅ | CH₃ | COCH₃ | COC₂H₅ |
| CH₃ | C₂H₅ | COCH₃ | COC₂H₅ | C₂H₅ | C₂H₅ | COCH₃ | COC₂H₅ |
| CH₃ | H | COC₂H₅ | COC₂H₅ | C₂H₅ | H | COC₂H₅ | COC₂H₅ |
| CH₃ | CH₃ | COC₂H₅ | COC₂H₅ | C₂H₅ | CH₃ | COC₂H₅ | COC₂H₅ |
| CH₃ | C₂H₅ | COC₂H₅ | COC₂H₅ | C₂H₅ | C₂H₅ | COC₂H₅ | COC₂H₅ |
| CH₃ | H | CN | COC₂H₅ | C₂H₅ | H | CN | COC₂H₅ |
| CH₃ | CH₃ | CN | COC₂H₅ | C₂H₅ | CH₃ | CN | COC₂H₅ |

TABLE 3-continued

| | | | | | | | |
|---|---|---|---|---|---|---|---|
| CH₃ | C₂H₅ | CN | COC₂H₅ | C₂H₅ | C₂H₅ | CN | COC₂H₅ |
| CH₃ | H | CONH₂ | COC₂H₅ | C₂H₅ | H | CONH₂ | COC₂H₅ |
| CH₃ | CH₃ | CONH₂ | COC₂H₅ | C₂H₅ | CH₃ | CONH₂ | COC₂H₅ |
| CH₃ | C₂H₅ | CONH₂ | COC₂H₅ | C₂H₅ | C₂H₅ | CONH₂ | COC₂H₅ |
| CH₃ | H | H | H | C₂H₅ | H | H | H |
| CH₃ | CH₃ | H | H | C₂H₅ | CH₃ | H | H |
| CH₃ | C₂H₅ | H | H | C₂H₅ | C₂H₅ | H | H |
| CH₃ | H | COOCH₃ | H | C₂H₅ | H | COOCH₃ | H |
| CH₃ | CH₃ | COOCH₃ | H | C₂H₅ | CH₃ | COOCH₃ | H |
| CH₃ | C₂H₅ | COOCH₃ | H | C₂H₅ | C₂H₅ | COOCH₃ | H |
| CH₃ | H | COOC₂H₅ | H | C₂H₅ | H | COOC₂H₅ | H |
| CH₃ | CH₃ | COOC₂H₅ | H | C₂H₅ | CH₃ | COOC₂H₅ | H |
| CH₃ | C₂H₅ | COOC₂H₅ | H | C₂H₅ | C₂H₅ | COOC₂H₅ | H |
| CH₃ | H | COCH₃ | H | C₂H₅ | H | COCH₃ | H |
| CH₃ | CH₃ | COCH₃ | H | C₂H₅ | CH₃ | COCH₃ | H |
| CH₃ | C₂H₅ | COCH₃ | H | C₂H₅ | C₂H₅ | COCH₃ | H |
| CH₃ | H | COC₂H₅ | H | C₂H₅ | H | COC₂H₅ | H |
| CH₃ | CH₃ | COC₂H₅ | H | C₂H₅ | CH₃ | COC₂H₅ | H |
| CH₃ | C₂H₅ | COC₂H₅ | H | C₂H₅ | C₂H₅ | COC₂H₅ | H |
| CH₃ | H | CN | H | C₂H₅ | H | CN | H |
| CH₃ | CH₃ | CN | H | C₂H₅ | CH₃ | CN | H |
| CH₃ | C₂H₅ | CN | H | C₂H₅ | C₂H₅ | CN | H |
| CH₃ | H | CONH₂ | H | C₂H₅ | H | CONH₂ | H |
| CH₃ | CH₃ | CONH₂ | H | C₂H₅ | CH₃ | CONH₂ | H |
| CH₃ | C₂H₅ | CONH₂ | H | C₂H₅ | C₂H₅ | CONH₂ | H |
| CH₃ | H | H | COOCH₃ | C₂H₅ | H | H | COOCH₃ |
| CH₃ | CH₃ | H | COOCH₃ | C₂H₅ | CH₃ | H | COOCH₃ |
| CH₃ | C₂H₅ | H | COOCH₃ | C₂H₅ | C₂H₅ | H | COOCH₃ |
| CH₃ | H | COOCH₃ | COOCH₃ | C₂H₅ | H | COOCH₃ | COOCH₃ |
| CH₃ | CH₃ | COOCH₃ | COOCH₃ | C₂H₅ | CH₃ | COOCH₃ | COOCH₃ |
| CH₃ | C₂H₅ | COOCH₃ | COOCH₃ | C₂H₅ | C₂H₅ | COOCH₃ | COOCH₃ |
| CH₃ | H | COOC₂H₅ | COOCH₃ | C₂H₅ | H | COOC₂H₅ | COOCH₃ |
| CH₃ | CH₃ | COOC₂H₅ | COOCH₃ | C₂H₅ | CH₃ | COOC₂H₅ | COOCH₃ |
| CH₃ | C₂H₅ | COOC₂H₅ | COOCH₃ | C₂H₅ | C₂H₅ | COOC₂H₅ | COOCH₃ |
| CH₃ | H | COCH₃ | COOCH₃ | C₂H₅ | H | COCH₃ | COOCH₃ |
| CH₃ | CH₃ | COCH₃ | COOCH₃ | C₂H₅ | CH₃ | COCH₃ | COOCH₃ |
| CH₃ | C₂H₅ | COCH₃ | COOCH₃ | C₂H₅ | C₂H₅ | COCH₃ | COOCH₃ |
| CH₃ | H | COC₂H₅ | COOCH₃ | C₂H₅ | H | COC₂H₅ | COOCH₃ |
| CH₃ | CH₃ | COC₂H₅ | COOCH₃ | C₂H₅ | CH₃ | COC₂H₅ | COOCH₃ |
| CH₃ | C₂H₅ | COC₂H₅ | COOCH₃ | C₂H₅ | C₂H₅ | COC₂H₅ | COOCH₃ |
| CH₃ | H | CN | COOCH₃ | C₂H₅ | H | CN | COOCH₃ |
| CH₃ | CH₃ | CN | COOCH₃ | C₂H₅ | CH₃ | CN | COOCH₃ |
| CH₃ | C₂H₅ | CN | COOCH₃ | C₂H₅ | C₂H₅ | CN | COOCH₃ |
| CH₃ | H | CONH₂ | COOCH₃ | C₂H₅ | H | CONH₂ | COOCH₃ |
| CH₃ | CH₃ | CONH₂ | COOCH₃ | C₂H₅ | CH₃ | CONH₂ | COOCH₃ |
| CH₃ | C₂H₅ | CONH₂ | COOCH₃ | C₂H₅ | C₂H₅ | CONH₂ | COOCH₃ |
| CH₃ | H | H | COOC₂H₅ | C₂H₅ | H | H | COOC₂H₅ |
| CH₃ | CH₃ | H | COOC₂H₅ | C₂H₅ | CH₃ | H | COOC₂H₅ |
| CH₃ | C₂H₅ | H | COOC₂H₅ | C₂H₅ | C₂H₅ | H | COOC₂H₅ |
| CH₃ | H | COOCH₃ | COOC₂H₅ | C₂H₅ | H | COOCH₃ | COOC₂H₅ |
| CH₃ | CH₃ | COOCH₃ | COOC₂H₅ | C₂H₅ | CH₃ | COOCH₃ | COOC₂H₅ |
| CH₃ | C₂H₅ | COOCH₃ | COOC₂H₅ | C₂H₅ | C₂H₅ | COOCH₃ | COOC₂H₅ |
| CH₃ | H | COOC₂H₅ | COOC₂H₅ | C₂H₅ | H | COOC₂H₅ | COOC₂H₅ |
| CH₃ | CH₃ | COOC₂H₅ | COOC₂H₅ | C₂H₅ | CH₃ | COOC₂H₅ | COOC₂H₅ |
| CH₃ | C₂H₅ | COOC₂H₅ | COOC₂H₅ | C₂H₅ | C₂H₅ | COOC₂H₅ | COOC₂H₅ |
| CH₃ | H | COCH₃ | COOC₂H₅ | C₂H₅ | H | COCH₃ | COOC₂H₅ |
| CH₃ | CH₃ | COCH₃ | COOC₂H₅ | C₂H₅ | CH₃ | COCH₃ | COOC₂H₅ |
| CH₃ | C₂H₅ | COCH₃ | COOC₂H₅ | C₂H₅ | C₂H₅ | COCH₃ | COOC₂H₅ |
| CH₃ | H | COC₂H₅ | COOC₂H₅ | C₂H₅ | H | COC₂H₅ | COOC₂H₅ |
| CH₃ | CH₃ | COC₂H₅ | COOC₂H₅ | C₂H₅ | CH₃ | COC₂H₅ | COOC₂H₅ |
| CH₃ | C₂H₅ | COC₂H₅ | COOC₂H₅ | C₂H₅ | C₂H₅ | COC₂H₅ | COOC₂H₅ |
| CH₃ | H | CN | COOC₂H₅ | C₂H₅ | H | CN | COOC₂H₅ |
| CH₃ | CH₃ | CN | COOC₂H₅ | C₂H₅ | CH₃ | CN | COOC₂H₅ |
| CH₃ | C₂H₅ | CN | COOC₂H₅ | C₂H₅ | C₂H₅ | CN | COOC₂H₅ |
| CH₃ | H | CONH₂ | COOC₂H₅ | C₂H₅ | H | CONH₂ | COOC₂H₅ |
| CH₃ | CH₃ | CONH₂ | COOC₂H₅ | C₂H₅ | CH₃ | CONH₂ | COOC₂H₅ |
| CH₃ | C₂H₅ | CONH₂ | COOC₂H₅ | C₂H₅ | C₂H₅ | CONH₂ | COOC₂H₅ |

APPLICABILITY IN INDUSTRY

As described above, the present invention provides novel thiophenol compounds substituted with hetero rings, which are useful as intermediates for agrochemicals and medicines, and intermediates to produce them. With the use of easily available enol lactone derivatives as starting materials, the processes of this invention can produce the cyclohexenone compounds and thiophenol compounds substituted with hetero rings of the present invention simply, in high yield and at low cost.

The compounds of the present invention are useful as intermediates to produce medicines and agrochemicals, particularly as intermediates for compounds with herbicidal activities for example, pyrazole derivatives with herbicidal activities, described in WO 97/41118 and others, may be produced by using the compounds (represented by Formula (1)) of the present invention as intermediates, as shown in the following reaction scheme.

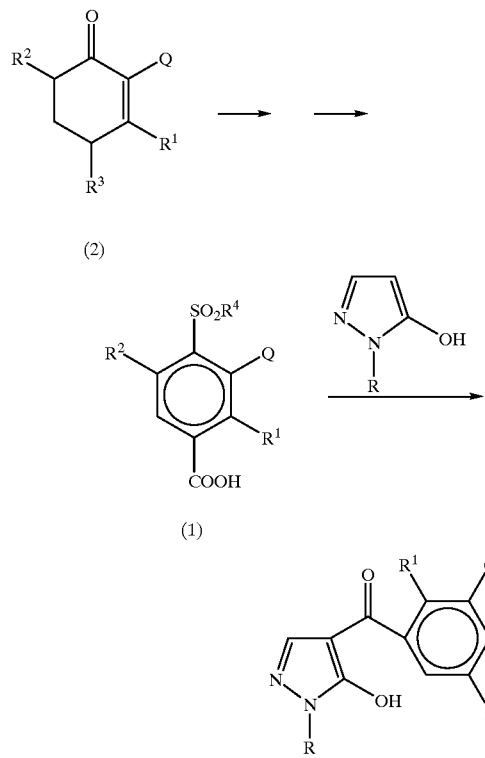

What is claimed is:

1. A thiophenol derivative substituted with a hetero ring, represented by Formula (1)

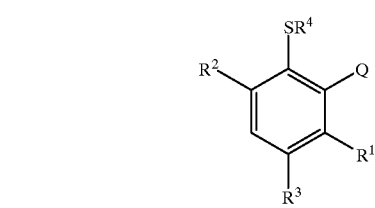

(1)

wherein $R^1$ is $C_{1-4}$ alkyl;

$R^2$ is selected from the group consisting of hydrogen and $C_{1-4}$ alkyl;

$R^3$ is selected from the group consisting of hydrogen, cyano, amide, $C_{1-4}$ alkylcarbonyl and $C_{1-4}$ alkoxycarbonyl;

$R^4$ is $C_{1-4}$ alkyl; and

Q is selected from the group consisting of Q1, Q2 and Q3

Q1:

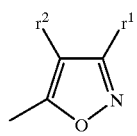

Q2:

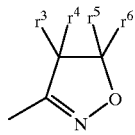

Q3:

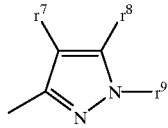

wherein $r^1$ to $r^9$ are, each independently, hydrogen or $C_{1-4}$ alkyl, or $r^3$ and $r^5$ may join to form a bond.

2. A cyclohexenone derivative represented by Formula (2)

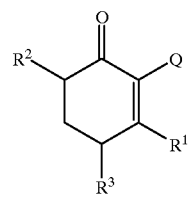

(2)

wherein $R^1$ is $C_{1-4}$ alkyl;

$R^2$ is selected from the group consisting of hydrogen and $C_{1-4}$ alkyl;

$R^3$ is selected from the group consisting of hydrogen, cyano, amide, $C_{1-4}$ alkylcarbonyl and $C_{1-4}$ alkoxycarbonyl; and Q is selected from the group consisting of Q1, Q2 and Q3

Q1:

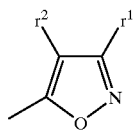

Q2:

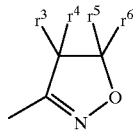

Q3:

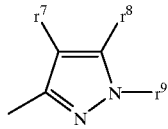

wherein $r^1$ to $r^9$ are, each independently, hydrogen or $C_{1-4}$ alkyl, or $r^3$ and $r^5$ may join to form a bond.

3. A process for the preparation of thiophenol derivatives substituted with a hetero ring, represented by Formula (1)

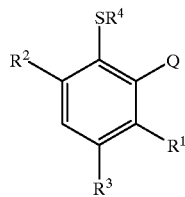

(1)

wherein R¹ is $C_{1-4}$ alkyl;

R² is selected from the group consisting of hydrogen and $C_{1-4}$ alkyl;

R³ is selected from the group consisting of hydrogen, cyano, amide, $C_{1-4}$ alkylcarbonyl and $C_{1-4}$ alkoxycarbonyl;

R⁴ is $C_{1-4}$ alkyl; and

Q is selected from the group consisting of Q1, Q2 and Q3

Q1:
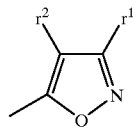

Q2:
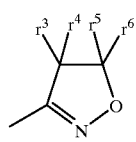

Q3:
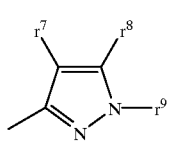

wherein r¹ to r⁹ are, each independently, hydrogen or $C_{1-4}$ alkyl, or r³ and r⁵ may join to form a bond;

characterized in that a compound of Formula (2)

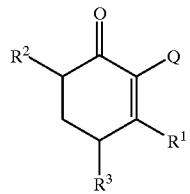

(2)

wherein R¹ is $C_{1-4}$ alkyl;

R² is selected from the group consisting of hydrogen and $C_{1-4}$ alkyl;

R³ is selected from the group consisting of hydrogen, cyano, amide, $C_{1-4}$ alkylcarbonyl and $C_{1-4}$ alkoxycarbonyl; and R⁴ is $C_{1-4}$ alkyl; and Q is selected from the group consisting of Q1, Q2 and Q3

Q1:
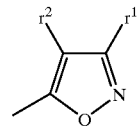

Q2:
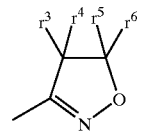

Q3:
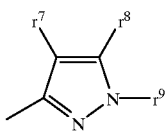

wherein r¹ to r⁹ are, each independently, hydrogen or $C_{1-4}$ alkyl, or r³ and r⁵ may join to form a bond;

is reacted with an alkane thiol of Formula R⁴SH wherein R⁴ is $C_{1-4}$ alkyl; to provide a compound of Formula (3)

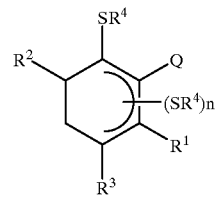

(3)

wherein R¹ is $C_{1-4}$ alkyl;

R² isselected from the group consisting of hydrogen and $C_{1-4}$ alkyl;

R³ is selected from the group consisting of hydrogen, cyano, amide, $C_{1-4}$ alkylcarbonyl and $C_{1-4}$ alkoxycarbonyl;

R⁴ is $C_{1-4}$ alkyl; and

Q is selected from the group consisting of Q1, Q2 and Q3

Q1:
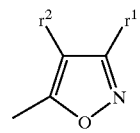

Q2:
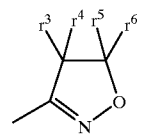

Q3:
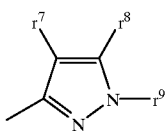

wherein r¹ to r⁹ are, each independently, hydrogen or $C_{1-4}$ alkyl, or r³ and r⁵ may join to form a bond;

n is 0, 1 or 2; and the compound of Formula (3) is selected from the group consisting of Formula (3-1), (3-2), (3-3) and (3-4))

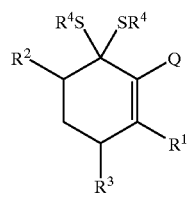
(3-1)

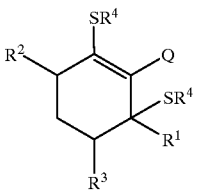
(3-2)

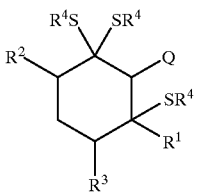
(3-3)

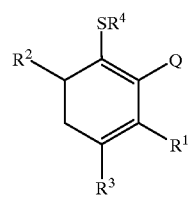
(3-4)

followed by dehydrogenation.

4. A compound represented by Formula (4)

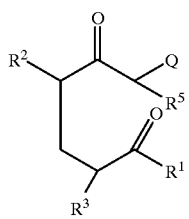
(4)

wherein $R^1$ is $C_{1-4}$ alkyl;

$R^2$ is selected from the group consisting of hydrogen and $C_{1-4}$ alkyl;

$R^3$ is selected from the group consisting of hydrogen, cyano, amide, $C_{1-4}$ alkylcarbonyl and $C_{1-4}$ alkoxycarbonyl; and $R^5$ is selected from the group consisting of hydrogen, cyano, $C_{1-4}$ alkylcarbonyl and $C_{1-4}$ alkoxycarbonyl; and Q is selected from the group consisting of Q1, Q2 and Q3

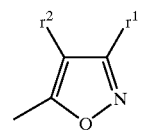
Q1:

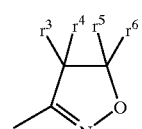
Q2:

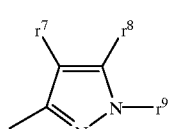
Q3:

wherein $r^1$ to $r^9$ are, each independently, hydrogen or $C_{1-4}$ alkyl, or $r^3$ and $r^5$ may join to form a bond.

5. A process for the preparation of a compound of Formula (4)

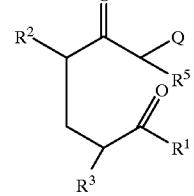
(4)

wherein $R^1$ is $C_{1-4}$ alkyl;

$R^2$ is selected from the group consisting of hydrogen and $C_{1-4}$ alkyl;

$R^3$ is selected from the group consisting of hydrogen, cyano, amide, $C_{1-4}$ alkylcarbonyl and $C_{1-4}$ alkoxycarbonyl;

$R^5$ is selected from the group consisting of hydrogen, cyano, $C_{1-4}$ alkylcarbonyl and $C_{1-4}$ alkoxycarbonyl; and Q is selected from the group consisting of Q1, Q2 and Q3

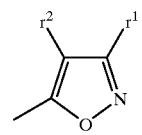
Q1:

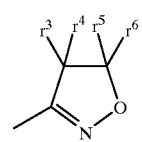
Q2:

-continued

Q3: 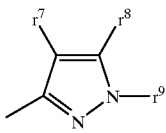

wherein $r^1$ to $r^9$ are, each independently, hydrogen or $C_{1-4}$ alkyl, or $r^3$ and $r^5$ may join to form a bond;

characterized in that an enol lactone of Formula (5)

(5)
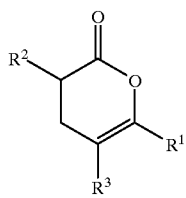

wherein $R^1$ is $C_{1-4}$ alkyl;

$R^2$ is selected from the group consisting of hydrogen and $C_{1-4}$ alkyl;

$R^3$ is selected from the group consisting of hydrogen, cyano, amide, $C_{1-4}$ alkylcarbonyl and $C_{1-4}$ alkoxycarbonyl;

is reacted with a compound of Formula Q—CH$_2$R$^5$ wherein Q is selected from the group consisting of Q1, Q2 and Q3

Q1: 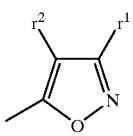

Q2: 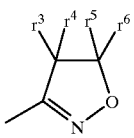

Q3: 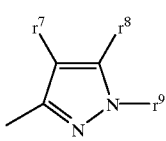

wherein $r^1$ to $r^9$ are, each independently, hydrogen or $C_{1-4}$ alkyl, or $r^3$ and $r^5$ may join to form a bond; and $R^5$ is selected from the group consisting of hydrogen, cyano, $C_{1-4}$ alkylcarbonyl and $C_{1-4}$ alkoxycarbonyl.

6. A process for the preparation of a compound of Formula (2)

(2)
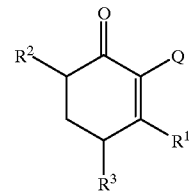

wherein $R^1$ is $C_{1-4}$ alkyl;

$R^2$ is selected from the group consisting of hydrogen and $C_{1-4}$ alkyl;

$R^3$ is selected from the group consisting of hydrogen, cyano, amide, $C_{1-4}$ alkylcarbonyl and $C_{1-4}$ alkoxycarbonyl; and Q is selected from the group consisting of Q1, Q2 and Q3

Q1: 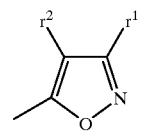

Q2: 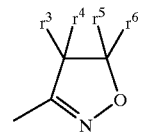

Q3: 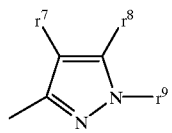

wherein $r^1$ to $r^9$ are, each independently, hydrogen or $C_{1-4}$ alkyl, or $r^3$ and $r^5$ may join to form a bond;

characterized in that an acid or a base is reacted on a compound of Formula (4)

(4)
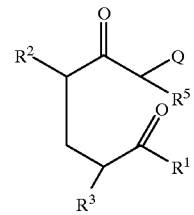

wherein $R^1$ is $C_{1-4}$ alkyl;

$R^2$ is selected from the group consisting of hydrogen and $C_{1-4}$ alkyl;

$R^3$ is selected from the group consisting of hydrogen, cyano, amide, $C_{1-4}$ alkylcarbonyl and $C_{1-4}$ alkoxycarbonyl;

$R^5$ is selected from the group consisting of hydrogen, cyano, $C_{1-4}$ alkylcarbonyl and $C_{1-4}$ alkoxycarbonyl; and Q is selected from the group consisting of Q1, Q2 and Q3
Q1:
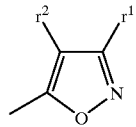
Q2:
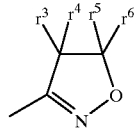
Q3:
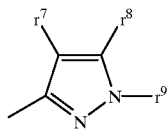
wherein $r^1$ to $r^9$ are, each independently, hydrogen or $C_{1-4}$ alkyl, or $r^3$ and $r^5$ may join to form a bond.
* * * * *

UNITED STATES PATENT AND TRADEMARK OFFICE
CERTIFICATE OF CORRECTION

PATENT NO. : 6,359,143 B1
DATED : March 19, 2002
INVENTOR(S) : Hiroyuki Adachi et al.

It is certified that error appears in the above-identified patent and that said Letters Patent is hereby corrected as shown below:

Title page,
Item [75], Inventors, replace "city of first inventor" with -- Kanagawa --.
Item [75], Inventors, replace "city of second inventor" with -- Niigata --.
Item [75], Inventors, replace "city of third inventor" with -- Kanagawa --.

Column 5,
Line 44, replace "3-ethyl-isooxazol-$^5$-yl," with -- 3-ethyl-isooxazol,-5-yl, --.

Column 6,
Line 1, replace Formula (1) with --

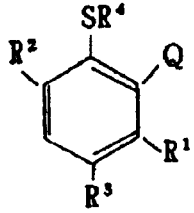

(1)

UNITED STATES PATENT AND TRADEMARK OFFICE
CERTIFICATE OF CORRECTION

PATENT NO.    : 6,359,143 B1
DATED         : March 19, 2002
INVENTOR(S)   : Hiroyuki Adachi et al.

It is certified that error appears in the above-identified patent and that said Letters Patent is hereby corrected as shown below:

Column 11,
Line 33 replace [Compound (3)-1] with --

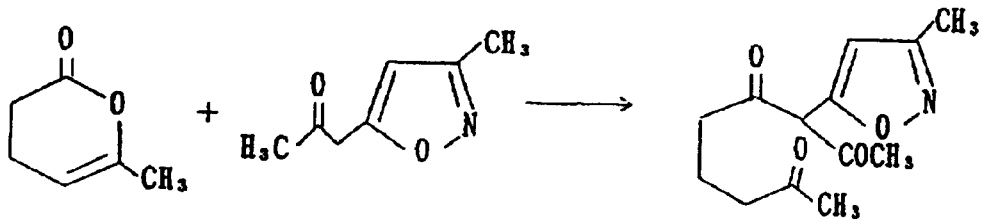

Column 13,
Line 26, replace "(s,31H)," with -- (s,3H), --.

Column 23,
Line 37, replace "derivative" with -- compound --.

Column 24,
Line 18, replace "may join to" with -- when joined --.
Line 20, replace "derivative" with -- compound --.
Line 64, replace "may join to" with-- when joined --.
Line 66, replace "thiophenol derivatives" with -- a thiophenol compound --.

Column 25,
Line 46, replace "may join to" with -- when joined --.
Line 48, replace "characterized in that" with -- by reacting --.

Column 26,
Line 23, replace "may join to" with -- when joined --.
Line 24, replace "is reacted with an alkane thiol" with -- with an alkane thiol --.
Line 39, replace "isselected" with -- is selected --.
Line 67, replace "may join to" with -- when joined --.

UNITED STATES PATENT AND TRADEMARK OFFICE
CERTIFICATE OF CORRECTION

PATENT NO.   : 6,359,143 B1
DATED        : March 19, 2002
INVENTOR(S)  : Hiroyuki Adachi et al.

It is certified that error appears in the above-identified patent and that said Letters Patent is hereby corrected as shown below:

<u>Column 28,</u>
Line 25, replace "may join to" with -- when joined --.

<u>Column 29,</u>
Line 11, replace "may join to" with -- when joined --.
Line 14, replace "characterized in that" with -- by reacting --.
Line 35, replace "is reacted with a compound" with -- with a compound --.
Line 61, replace "may join to" with -- when joined --.

<u>Column 30,</u>
Line 42, replace "may join to" with -- when joined --.
Line 43, replace "characterized in that an acid or base is reacted on a" with -- by reacting an acid or a base on a --.

<u>Column 32,</u>
Line 12, replace "may join to" with -- when joined --.

Signed and Sealed this

Twenty-seventh Day of August, 2002

*Attest:*

*Attesting Officer*

JAMES E. ROGAN
*Director of the United States Patent and Trademark Office*